(12) United States Patent
Schiffrin et al.

(10) Patent No.: US 6,905,679 B1
(45) Date of Patent: Jun. 14, 2005

(54) LACTIC ACID BACTERIA FOR THE TREATMENT AND/OR PROPHYLAXIS OF GIARDIASIS

(75) Inventors: Eduardo Schiffrin, Crissier (CH); Pablo Perez, La Plata (AR)

(73) Assignee: Nestec S.A., Vevey (CH)

( * ) Notice: Subject to any disclaimer, the term of this patent is extended or adjusted under 35 U.S.C. 154(b) by 155 days.

(21) Appl. No.: 10/111,258

(22) PCT Filed: Oct. 13, 2000

(86) PCT No.: PCT/EP00/10105

§ 371 (c)(1),
(2), (4) Date: Jul. 22, 2002

(87) PCT Pub. No.: WO01/30365

PCT Pub. Date: May 3, 2001

(30) Foreign Application Priority Data

Oct. 26, 1999 (EP) .......................................... 99121356

(51) Int. Cl.[7] .......................... A61K 48/00; A01N 65/00
(52) U.S. Cl. ................... 424/93.4; 424/93.45; 424/408; 424/439; 424/450
(58) Field of Search ............................ 424/93.4, 93.45, 424/408, 439, 450

(56) References Cited

U.S. PATENT DOCUMENTS 5,603,930 A * 2/1997 Brassart et al. .......... 424/93.45

FOREIGN PATENT DOCUMENTS

| EP | 0 577 904 A1 | 1/1994 |
|---|---|---|
| WO | WO 96/29083 | 9/1996 |
| WO | WO 97/35596 | 10/1997 |
| WO | WO 01/30365 | 5/2001 |

OTHER PUBLICATIONS

Thompson et al. article entitled "Nomenclature and Genetic Groupings of *Giardia* Infecting Mammals" *Parasitology Today*, vol. 16, No. 5, 2000, pp. 210–213.

Rasic et al. article entitled "Bifidobacteria and Their Role" 1983, pp. 86–101.

Reiner et al. article entitled "Human Milk Kills *Giardia lamblia* by Generating Toxic Lipolytic Products" *The Journal of Infectious Diseases*, vol. 154, No. 5, Nov. 1986, pp. 835–832.

Chavez et al., "*Giardia lamblia*; In Vitro Cytopathic Effect of Human Isolates" Experimental Parasitology 80, 1995, pp. 133–138.

Buret et al., "Pathophysiology of Small Intestinal Malabsorption in Gerbils Infected With *Giardia lamblia*," Gastroenterology 103, 1992, pp. 506–513.

Roberts–Thomson, et al., "Giardiasis in the Mouse: An Animal Model" Gastroenterology 71, 1976, pp. 57–61.

Aley et al., "Specialized Surface Adaptations of *Giardia lamblia*" Infectious Agents and Disease, 4, 1995, pp. 161–166.

Muller et al., "Serological Analysis of Antigenic Heterogeneity of *Giardia lamblia* Variant Surface Proteins" Infection and Immunity, 64, 1996, pp. 1385–1390.

Nash et al., "*Giardia lamblia:* Identification and Characterization of a Variant–Specific Surface Protein Gene Family" J. Euk. Microbiol., 42, 1995, pp. 604–609.

Gillin et al., "Cell Biology of the Primitive Eukaryote *Giardia Lamblia*" Annu. Rev. Microbiol. 50, 1996, pp. 679–705.

Katelaris et al., "Activity of metronidazole, azithromycin and three benzimidazoles on *Giardia lamblia* growth and attachment to a human intestinal cell line" Altment Pharmacol. Ther. 8, 1994, pp. 187–192.

* cited by examiner

*Primary Examiner*—Herbert J. Lilling
(74) *Attorney, Agent, or Firm*—Bell, Boyd & Lloyd LLC

(57) ABSTRACT

The present invention relates to the use of a supernatant of lactic acid bacteria or of Bifidobacteria capable of preventing colonization of intestinal cells by *Giardia intestinalis*, for the preparation of an ingestable carrier for the treatment and/or prophylaxis of disorders associated with the colonization of the gut by *Giardia intestinalis*. The present invention also pertains to specific strains of Bifidobacterium having the above traits and to the ingestable carrier, such as a food or pharmaceutical composition containing such supernatant or the microorganisms.

12 Claims, 10 Drawing Sheets added. Results are means of three determinations

LACTIC ACID BACTERIA FOR THE TREATMENT AND/OR PROPHYLAXIS OF GIARDIASIS

BACKGROUND OF THE INVENTION

The present invention relates to lactic acid bacteria capable of preventing colonization of intestinal cells by *Giardia intestinalis*, or to a culture supernatant thereof, respectively, for use in the treatment and/or prophylaxis of disorders associated with the colonization of the gut by *Giardia intestinalis*. The present invention also pertains to strains of *Bifidobacterium* having the above traits and to the use of lactic acid bacteria for the preparation of an ingestable carrier, such as a food or pharmaceutical composition, for the treatment and/or prophylaxis of an infestation of the intestine by *Giardia intestinalis*.

*Giardia intestinalis* is a flagellate protozoan which upon infestation of an individual's gut may effect disorders such as abdominal pains, loose stool or even severe diarrhea. Its life cycle has two stages, cysts and trophozoites, which different forms allow the microorganism to survive in different and even adverse environments.

Cysts are dormant, quadrinucleate and ovoid forms responsible for transmission of giardiasis. After ingestion of cysts by an individual, excystation is triggered by exposure to gastric acid and/or digestive enzymes. The parasite thus emerging, which is termed trophozoite, is binucleate and half-pear shaped having a size of around 10 $\mu$m with a broad anterior and a narrow posterior side. The ventral side is by and large covered by the ventral disk which is deemed to at least in part account for an attachment of the trophozoite to the intestinal surface After excystation trophozoites may persist in the small intestine of the infected individuum for a long time amounting even to years. If trophozoites are carried downstream by the flow of intestinal fluid they again start to encyst to adapt to a new environment.

Cysts are excreted with the faeces and may withstand a variety of extreme environmental conditions, including different temperature, pH and tonicity conditions. An infected individual may secrete about $9 \times 10^8$ cysts per day, with doses to as low as 10 cysts proved to be sufficient to produce infection in another individual. Transmission of *Giardia intestinalis* may be accomplished in a variety of different ways with the main routes of transmission being waterborne and foodborne. Person to person spread is supported by some daycare and nosocomial outbreaks. In addition, wild animals are found to be infectious reservoirs of *Giardia intestinalis* and may contribute to a spread of the pathogen.

Giardiasis, like other intestinal diseases, is more severe in infants and children. Infection is normally associated with diarrhea and malabsorption resulting in an impaired growth and development of the child and may eventually also lead to the death of newbornes.

Around one half of infected people are, however, asymptomatic and contribute to the spread of the pathogen, since due to the absence of any perceptible symptoms no corresponding regimen is applied.

Though a great deal of scientific effort has been invested on the investigation of *Giardia intestinalis* pathogenesis of giardiasis could not be explained by means of a single virulence factor alone and no toxic compound has been isolated so far.

The light microscopic appearance of a gut colonized by *Giardia* has been found to be rather variable ranging from a normal mucosal structure to a subtotal villous atrophy. Results of electron microscopy investigations revealed ultrastructural changes such as shortening and disruption of microvilli (Chávez et al., Experimental Parasitol. 80 (1995), 133–138).

Such structural abnormalities have been found to be accompanied by a reduction in lactase, sucrase and maltase activities in the microvillus membrane as well as to an impaired intestinal transport (Buret et al., Gastroenterology 103 (1992), 506–513; Roberts-Thomson et al, Gastroenterology. 71 (1976), 57–61).

In addition to the two forms illustrated above *Giardia intestinalis* has developed an extremely changing surface structure and has evolved a family of protective proteins that cover all exposed surfaces (Aley et al., Infect. Agents Dis. 4 (1995), 161–166; Müller, et al., Infect. Immun. 64 (1996), 1385–1390; Nash et al., J. Euk. Microbiol. 42 (1995), 604–609). These variable surface proteins (VSPs) protect trophozoites from both immunological and environmental factors, such that *Giardia* may evade the host's defenses and may survive in a highly degradative environment such as is prevailing in the intestinal tract of mammals. A modification in the VSPs occurs at about every $6^{th}$ to $13^{th}$ generation making it difficult or nearly impossible for the host's immune system to develop a specific response against the pathogen. Immune and environmental stress can select different VSP phenotypes. Furthermore, antigen switching of VSPs after excystation has also been reported (Gillin et al., Annu. Rev. Microbiol. 50 (1996), 679–705).

Human giardiasis is associated with an increase in the number of lamina propria and intraepithelial lymphocytes suggesting that T-cell activation could be responsible for micro villous damage. However, induced immunosuppression in mice resulted in a more profound effect on microvillous associated enzymes as compared to non-immunosupressed animals, indicating that during an infection by *Giardia intestinalis* epithelial damage seems not be dependent on immune function alone.

A common therapy of giardiasis is the administration of antibiotics, such as those belonging to the class of nitroimidazoles. Yet, in endemic areas the response to therapy has been shown to be rather inconsistent (Katelaris et al., Aliment. Pharmacol. Ther. 8 (1994), 187–192). Moreover, due to the at least in part destruction of the intestine's natural microflora, the administration of such antibiotics is always accompanied by severe side effects such as extended diarrhea or even an expanded infestation of the gut by other detrimental microorganisms, such as yeast.

Hence, there is a need in the art for additional options to treat giardiasis or means to prevent infestation of an individual by the pathogen.

The problem of the present invention therefore resides in providing additional means for the treatment or prophylaxis of an infection by *Giardia intestinalis*.

SUMMARY OF THE INVENTION

This problem has been solved by providing the use of a culture supernatant of a Lactic acid bacteruim Lactic acid bacterium or a Bifidobacterium capable of preventing adhesion of *Giardia intestinalis* to intestinal cells for the preparation of an ingestable carrier for the treatment and/or prophylaxis of disorders associated with the colonization of the gut by *Giardia* intestinalis.

According to a preferred embodiment the present invention provides novel Lactic acid bacteria and Bifidobacteria, respectively, capable to prevent adhesion of *Giardia intestinalis* to intestinal cells, which are selected from the group consisting of NCC 90 (I-2332), NCC 189 (I-2333) or NCC 200 (I-2334). These microorganisms have been deposited according to the Budapest Treaty with the Institute Pasteur on Nov. 30$^{th}$, 1999 and received the above mentioned deposit numbers. The present invention pertains also to food and pharmaceutical compositions containing such microorganisms.

The microorganisms maybe included in the carrier in an amount of from about $10^6$ to about $10^{12}$ pfu (plaque forming units). They may be included as such or optionally after essentially purifying them from the cultivating medium. Alternatively, the supernatant of a culture of such microorganisms may be included in the carrier, which prior to its inclusion may preferably be concentrated by means well known in the art.

The ingestable carrier may be a food or a pharmaceutical composition such as milk, yogurt, curd, cheese, fermented milks, milk based fermented products, ice-creams, fermented cereal based products, milk based powders, infant formulae or any sort of pet food. Such carriers may e.g. be easily manufactured by using a microorganisms having the corresponding traits for fermentation of the starting materials itself. Alternatively, the microorganisms or an optionally concentrated culture supernatant thereof may be added to the respective carrier in liquid or dry form. A pharmaceutical composition, such as a tablet, a liquid bacterial suspension, a dried or wet oral supplement, a dry or a wet tube feeding may be prepared using standard techniques while including the microorganisms and/or an optionally concentrated culture supernatant thereof into the carrier. Depending on the mode of administration the skilled person will select the formulation deemed to be appropriate.

Additional features and advantages of the present invention will be described in and apparent from the detailed description of the invention and from the figures.

DETAILED DESCRIPTION OF THE INVENTION

Figure 1:
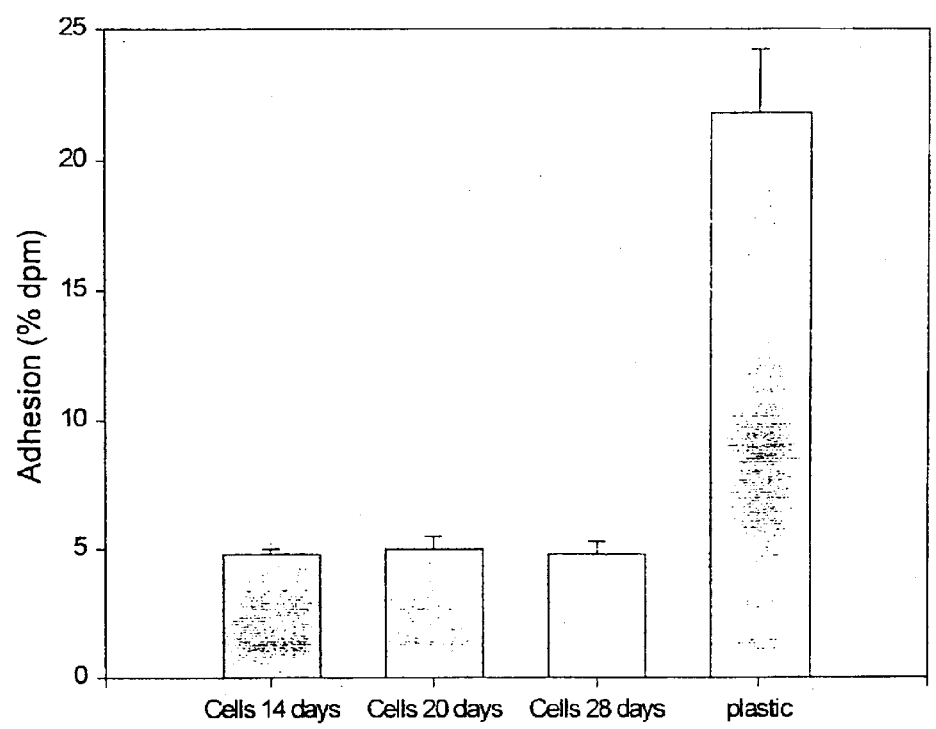
FIG. 1 shows adhesion of Portland-1 strain to Caco-2 cells when $10^5$ trophozoites/cm$^2$ were added.

During the studies leading to the present invention the inventors have hypothesized that an ecological approach in the treatment and/or prevention of giardiasis could be a colonization of the intestine with bacteria that might be able to antagonize with the parasite.

Attachment of *Giardia intestinalis* trophozoites to epithelial cells is deemed to be a key step for infection in humans and animals. Although the mechanisms for *Giardia* adhesion are not fully understood, evidence supports the ventral disk, trophozoite contractile elements, hydrodynamic and mechanical forces and lectin mediated binding to be involved.

Taking into account that lactic acid is an important factor in *Giardia*'s life cycle the interaction between *Giardia intestinalis* and lactic acid bacteria has been studied using enterocyte like cells in culture.

To this end, the following microbial parasite strains and culture media have been used:

Microbial Strains:

Bacterial strains La1 (*Lactobacillus johnsonii*) (I-1225) and La10 (*Lactobacillus acidophilus*) (I-2332) were from Nestec collection (Lausanne, Switzerland). Strains CIDCA 536 (*Bifidobacterium bifidum*) and CIDCA 538 (*Bifidobacterium infantis*) were from the collection of Centro de Investigación y Desarrollo en Criotecnología de Alimentos (Universidad Nacional de La Plata, Argentina) and have been deposited according to the Budapest Treaty receiving the deposit nos I2333 and i-2334,respectivley.

*Giardia intestinalis* stains Portland-1 (ATCC 30888), UNO/04/87/1 (ATCC 50184), New Orleans-1 (ATCC 50137) and WB (ATCC 30957) were purchased from American Type Culture Collection (Rockville, USA).

Bacteria were grown for 24 hours at 37° C. in MRS broth supplemented with 0,05% cysteine hydrochloride (Sigma). Incubations were performed under anaerobic conditions (BBL GasPak Plus).

Protozoa were grown in Keister's modified TYI-S-33 medium containing (per liter): casein digest (Difco), 20 g; yeast extract (BBL), 10 g; dextrose (Merck), 10 g; bovine bile (Difco), 0.75 g; NaCl (Merck), 2 g; L-cystein. HCl (Sigma), 2 g; ascorbic acid sodium salt (Fluka), 0.2 g; $K_2HPO_4$ (Merck), 1 g; $KH_2PO_4$ (Merck), 0.6 g; ferric ammonium citrate (Sigma), 22.8 mg, adult bovine serum (Sigma), 100 ml; penicillinlstreptomycin (Gibco, 1000 IU/ml, 1000 μg/ml), 15 ml. Horse serum (Gibco) instead of bovine serum was also assayed. The pH was adjusted to 6.9 with 1 N NaOH prior filter sterilization (0.22 μm pore size). Keister's modified medium supplemented with 10% horse serum did not support growth of strain Portland-1 although incubation was extended during 11 days and despite the fact that trophozoites were initially attached to the tube walls. During the first 5 days of incubation, an high proportion of motile parasites was observed. After this time agglutination of trophozoites and a dramatic decrease of viable cells were observed. Addition of bovine serum (10%) to these damaged cells allowed for growth after 24 hrs. To increase the surface available for *Giardia* attachment, 25 cm² tissue culture bottles were used (plastic bottles). Culture medium was added up to the bottleneck to maintain anaerobic conditions. This procedure resulted in yields of around 10⁷ trophozoites/bottle within 2–3 days of incubation and parasites formed a confluent monolayer on the bottle walls.

Subcultures were made by chilling cultures in an ice bath (5–10 min) to detach adhering trophozoites and inoculating 0.2 ml of the resulting suspension into fresh medium. Incubations were performed at 37° C. for 72 hours and different recipients (glass or plastic) were used.

Storage of *Giardia intestinalis* Stains:

Trophozoites were detached as indicated above and suspended in TYI-S-33 medium. Two fold concentrated cryoprotectant solution (DMSO, sucrose) prepared in TYI-S-33 medium, was added to the suspension in three equal aliquots at 2-minute intervals. Final concentrations of cryoprotectants were 12% (v/v) DMSO, 4% (w/v) sucrose. Suspensions (around $1 \times 10^6$ trophozoites/ml) were allowed to equilibrate during 20 minutes at room temperature before start of the cooling cycle.

Vials were thermally isolated with polystyrene (4 cm wall thickness) and placed at −80° C.

Reactivation of frozen Throphozoites:

Vials were thawn in a water bath at 37° C. and immediately inoculated in TYI-S-33 medium at a ratio parasite suspension/fresh medium=0.5/7. Cultures were incubated at 37° C. in the dark.

The present invention will now be illustrated by way of examples.

As a model for intestinal cells the cell lines Caco-2 and HT29 were used. Adhesion to said enterocyte like cells was tested as follows:

Example 1

Radiolabelling of Trophozoites

Parasites were inoculated in TYI-S-33 and 2.6 to 7.1 µCi/ml of either 2-³H adenine (21 Ci/mmol, 1 mCi/ml, Amersham Life Science) or methyl-³H thymidine (2 Ci/mmol, 1 mCi/ml, Amersham Life Science) were added. Incubations were performed at 37° C. for 48–72 hrs.

Growth of trophozoites with 7.1 µCi/ml of either ³H-adenine or ³H-thymidine gave very different DPM/parasite ratios (Table 1). Although thymidine concentration was 10-fold higher as compared to that of adenine, incorporation was very low with the result that 0.08 and 2.8 DPM/parasite were obtained, respectively.

TABLE 1

Incorporation of ³H by Giardia strain Portland-1
adding 7 µCi/ml of radiolabeled bases

| Radiolabeled substance | mmols/ml | DPM/parasite |
|---|---|---|
| 2-³H adenine | $3 \times 10^{-7}$ | 2.8 ± 0.10 |
| Methyl-³H thymidine | $35 \times 10^{-7}$ | 0.08 ± 0.00 |

Table 2 shows the results of the adenine incorporation by *Giardia intestinalis* strains. Suitable radiolabelling was obtained by using adenine concentrations as low as 2.5 µCi/ml. In these conditions, DPM/parasite ranged from 0.3 for Portland-1 strain to 1.6 for UNO strain.

TABLE 2

Incorporation of 2-³H adenine by different strains of Giardia
Results are averages of at least two determinations.

| | DPM per parasite | | |
|---|---|---|---|
| Strain | 7 µCi/ml | 5 µCi/ml | 2.5 µCi/ml |
| Portland-1 | 2.8 ± 0.1 | 0.9 ± 0.1 | 0.3 ± 0.0 |
| UNO | ND | 1.2 ± 0.2 | 1.6 ± 0.1 |
| WB | ND | 1.0 ± 0.2 | 1.4 ± 0.1 |
| New Orleans-1 | ND | 2.3 ± 0.8 | 0.6 ± 0.1 |

Example 2

Cell Cultivation

Caco-2 cells were grown in DMEM supplemented with non essential amino acids, penicillin (12 IU/ml), streptomycin (12 µg/ml), gentamicine (47 µg/ml) and inactivated fetal calf serum (20% v/v). Monolayers were prepared in 6-well tissue culture plates by seeding $2 \times 10^5$ cells per well. Incubations were performed at 37° C. in a 10% $CO_2$/90% air atmosphere. The culture medium was changed each $2^{nd}$ day. Adhesion assays were performed with cells between passages 49 and 51 and only monolayers in late postconfluence stage were used (at least two weeks in culture).

Undifferentiated HT-29 cells (American Type Culture Collection, Rockville, Md.) were grown in DMEM containing 4.5 g/l glucosa (Seromed, Biochrom KG, Berlin, Germany) supplemented with Glutamax 1 (0.01% v/v; L-alanyl-Lglutamine 200 mM, GIBCO, Basel, Switzerland), gentamycin (0.57 mg/ml, GIBCO, Basel, Switzerland) and fetal calf serum (10% v/v, GIBCO, Basel, Switzerland). Cells were used at passage 52.

Example 3

Adhesion Assays

When confluent monolayers of trophozoites were obtained, the culture medium was discarded, thus eliminating any parasites not attached to a surface. Attached parasites were harvested as described and washed 3 times with DMEM (Gibco) containing 11.4 mM cysteine HCl. Dilutions (1:2) of parasites in paraformaldehyde 1% were enumerated in an hemocytometer.

Radiolabelled trophozoites suspended in DMEM-CYS (DM EM+11.4 mM cysteine HCl) were added to monolayers of Caco-2 cells and incubated for 1 h at 37° C. in a 5% $CO_2$/95% air atmosphere. Monolayers were then washed 3 times with DMEM-CYS at 37° C. to detach unbound trophozoites.

After washing 1 ml of 1 N NaOH was added per well and the plates were incubated during 1 hr at room temperature. Cell lysates were placed in scintillation vials and a further wash of the wells with PBS was performed. Radioactivity was measured with a β-counter (RackBeta Spectral, LKB, Wallac).

Example 4

Preincubation Assays

Bacterial cultures were washed 3 times with PBS. Suspensions, that had been adjusted to $1 \times 10^8$ CFU/ml in DMEM, were added to Caco-2 monolayers and plates were incubated for 1 hr at 37° C. After adhesion of the bacterial suspensions radiolabelled trophozoites, adjusted to $1\times10^5$ parasites/ml, were added. Adhesions assays were performed as indicated above.

Example 5

Coincubation Assays 1 ml aliquots of parasitic suspensions containing $1\times10^5$ radiolabelled *Giardia* per ml were mixed with 1 ml of bacterial suspensions ($1\times10^8$ CFU/ml) in 6-well tissue culture plates containing Caco-2 monolayers. Adhesion assay were performed as indicated above.

Example 6

Action of Lactic Acid Bacteria Supernatants on Adhesion of *Giardia intestinalis*

Cultures of lactic acid bacteria were centrifuged at 900 g during 15 min and supernatants were neutralized (pH 6.9–7.4) with 4 N NaOH. 1 ml of a suspension containing $10^5$ radiolabelled trophozoites/ml in DMEM-CYS was mixed with 1 ml of neutralized supernatant in 6-well tissue culture plates containing Caco-2 monolayers. Adhesion assays were performed as indicated above. Appropriate controls with MRS or MRS acidified to pH 4.5 with lactic acid and then neutralized to pH 7 were included in the assays.

Preincubation assays were performed by incubating parasitic suspensions (DMEM-cys) with an equal volume of supernatant for 1 h at 37° C. In another series of experiments, parasites were suspended in pure supernatants or supernatants diluted with MRS. After incubation, giardias were suspended in DMEM and added to Caco-2 cells.

Assessment of growth was performed by incubating parasites in TYI-S-33 medium with 100 $\mu$Ci of $^3$H adenine in 40 ml of culture. Flow cytometric analysis was done using a blue-green excitation light (FACScan™).

Example 7

Scanning Electron Microscopy

Caco-2 cells were grown on round glass slides (diameter, 10 mm) into 24-well tissue culture plates and adhesion of trophozoites was done as indicated. Specimens were fixed by the addition of 2.5% glutaraldehyde in PBS for 16 h at 4° C. Post-fixation was performed with 2% osmium tetroxide at room temperature for 2 hrs and then smears were dehydrated in a graded series of ethanol solutions (solutions of ethanol in water of 30, 50, 70, 90, 100%). Finally, samples were critical point dried using $CO_2$, gold coated and examined using a Philips SEM 505 at an accelerating voltage of 30 KV.

Example 8

Adhesion of *Giardia intestinalis* Trophozoites to Caco-2 Cells

A total of $10^5$ trophozoites were added to a caco-2 culture prepared as detailed in example 2. The results of the adhesion assays are shown in FIG. 1. Adhesions of around 5% were obtained despite the age of the monolayers. Attachment to plastic surfaces was very high (21.8±2.4%).

Figure 2:
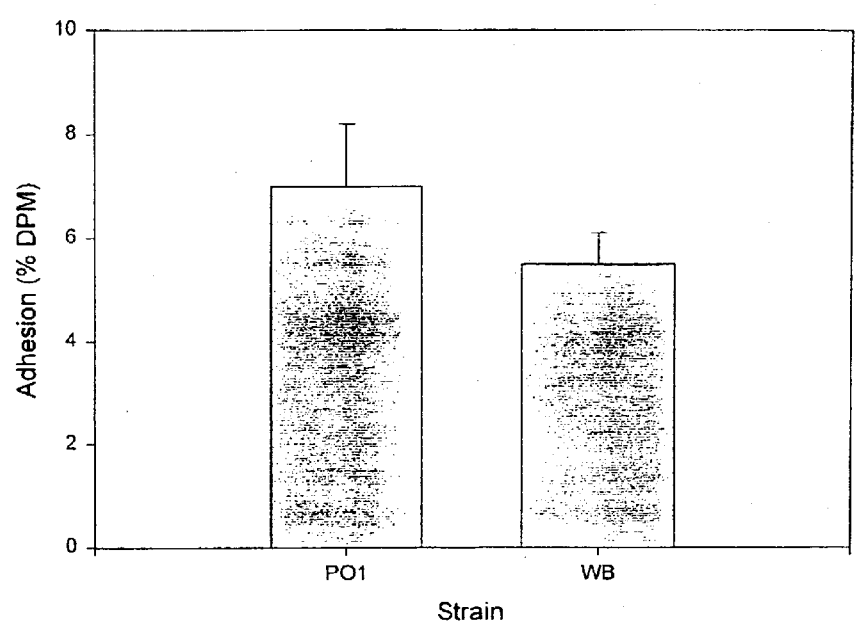
FIG. 2 shows the results of adhesion assays performed with undifferentiated HT-29 cells.
Figure 3:
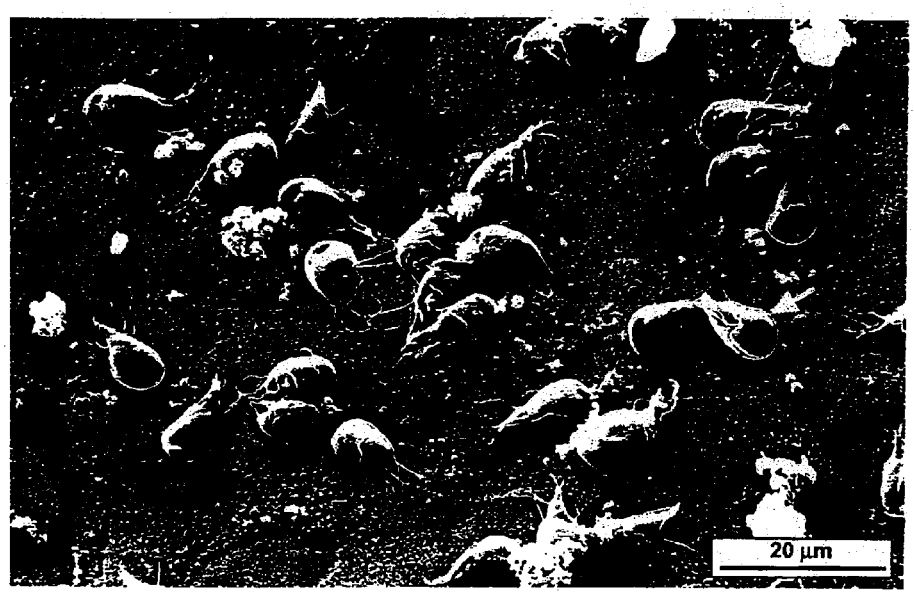
FIG. 3 shows a scanning electron micrography of strain UNO attached to differentiated Caco-2 cells.

The results of adhesion assays performed with undifferentiated HT-29 cells are shown in FIG. 2. Values of 7.0±1.2% and 5.5±0.6% were obtained for strains Portland-1 and WB respectively. Scanning electron micrography of stain UNO attached to differentiated Caco-2 cells is shown in FIG. 3. Most *Giardia* trophozoites are situated with the ventral side attached to the monolayer. Some parasites were also seen with their dorsal surface facing Caco-2 cells (arrow). As may be clearly derived from FIG. 4, attachment of trophozoites produces an imprint on the brush border of enterocyte like cells.

Figure 5:
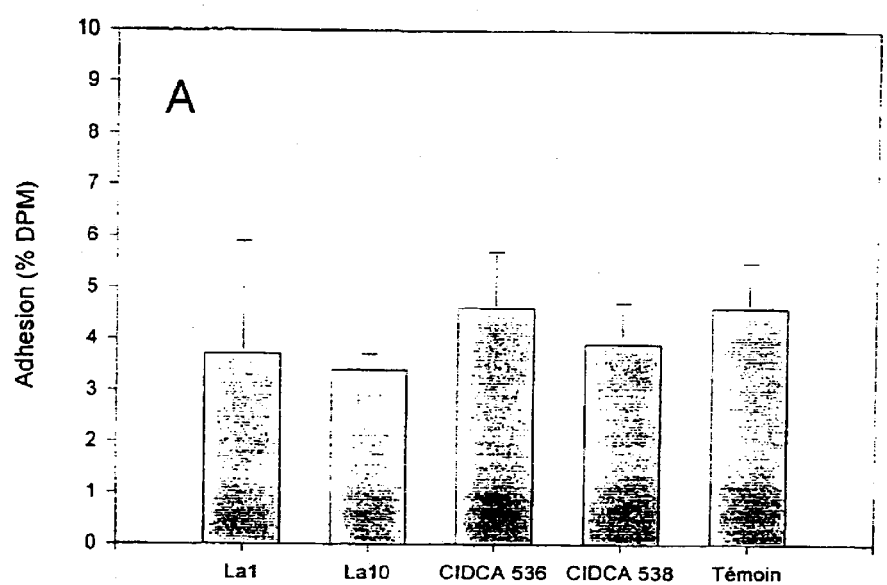
FIG. 5A shows the results of coincubation of giardias, lactic acid bacteria and Caco-2 cells.
FIG. 5B shows the results of preincubation of Caco-2 monolayers with lactic acid bacteria.
Figure 5:
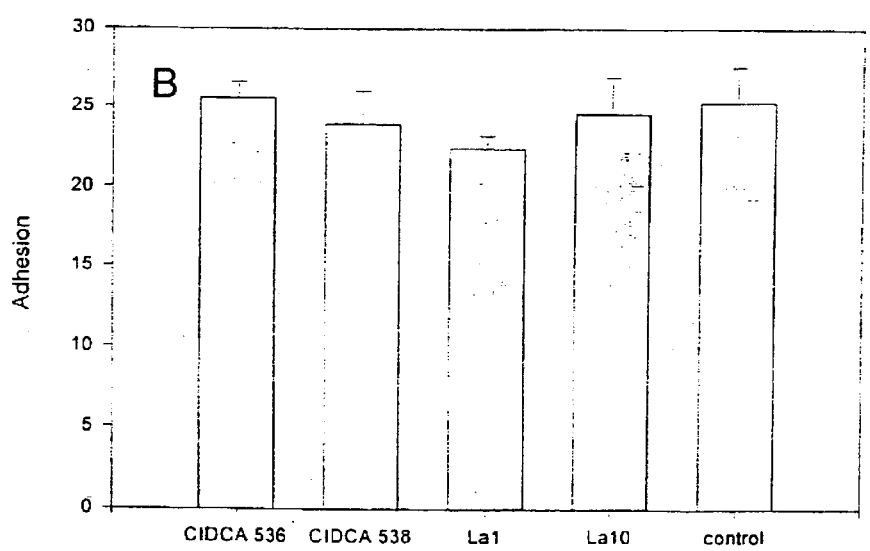

Coincubation of giardias, lactic acid bacteria and Caco-2 cells did not change attachment (FIG. 5A) Furthermore, preincubation of Caco-2 monolayers with lactic acid bacteria did not interfere with parasite adhesion (FIG. 5B).

Example 9

Figure 6:
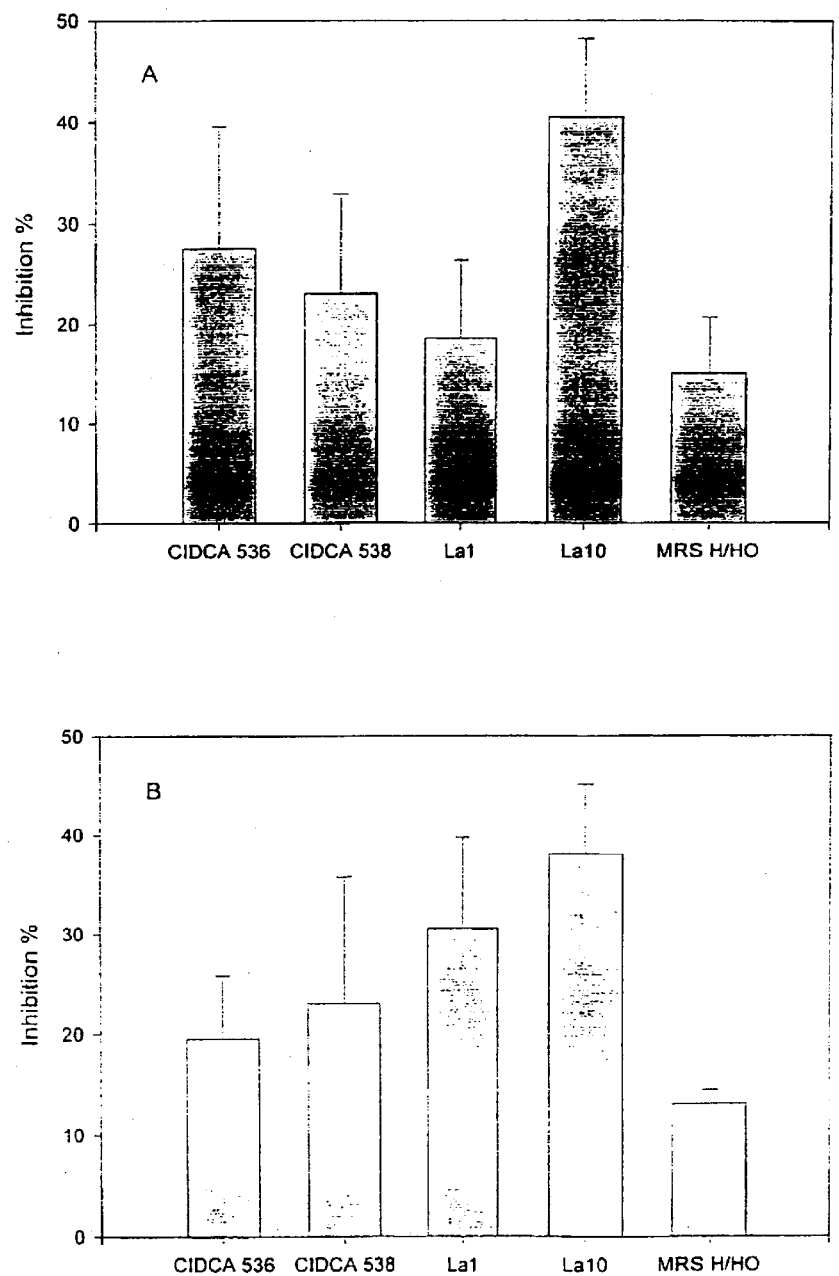
FIG. 6A shows the results of an adhesion experiment, wherein Portland-1 and WB were contacted with a neutralized supernatant of the lactic acid bacteria of the present invention.
FIG. 6B shows the results of an adhesion experiment, wherein WB and CIDCA were contacted with a neutralized supernatant of the lactic acid bacteria of the present invention.

Influence of Supernatants of Lactic Acid Bacteria Cultures on *Giardia intestinalis* Adhesion to Caco-2 Cells Coincubation of the strains Portland-1 and WB with neutralized supernatants of the lactic acid bacteria to be used according to the present invention produced a reduction of adhesion to Caco-2 cells ranging from 19% (La1 strain) to 40% (La10 strain) for Portland-1 strain (FIG. 6A). For strain WB, values ranged from 20% for strain CIDCA 536 to 40% for strain La10 (FIG. 6B). Although differences between the strains could not be established, strain La10 showed significant differences as compared to the MRS control for both, the Portland-1 (P=0,06) and the WB strain (P=0.04).

Figure 7:
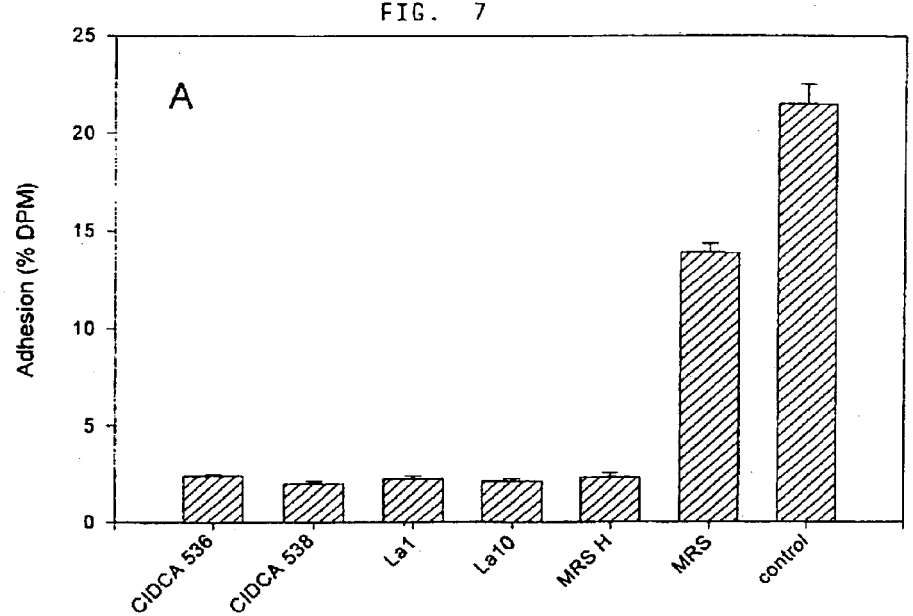
FIG. 7A shows the results obtained by incubating the strain WB with acid supernatants (pH 4) (DMEM:supernatant=1:1) during 1 hr.
FIG. 7B shows that neutralization of supernatants (pH 7) abolishes inhibitory effect.
Figure 7:
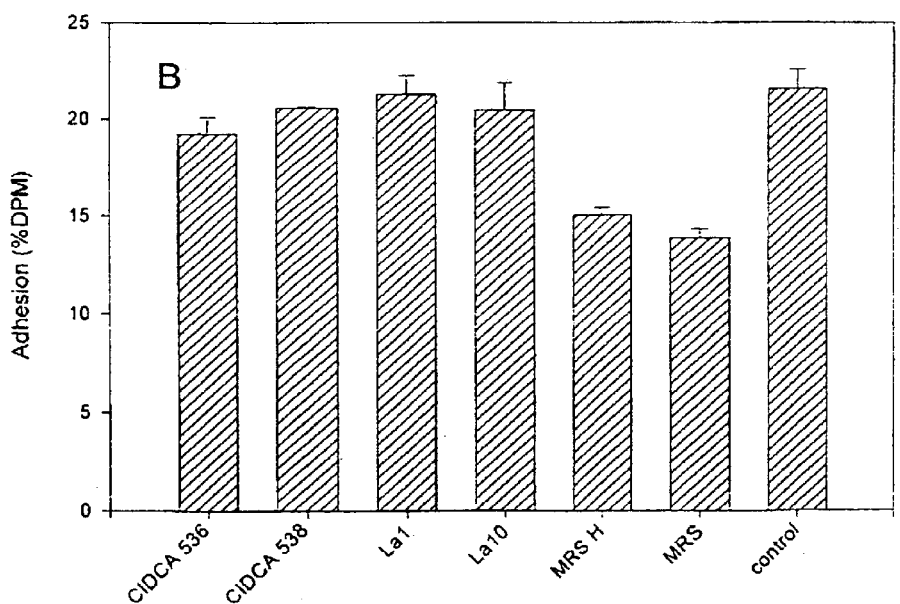

Taking into account that the range of pH compatible with the coincubation experiments with Caco-2 cells is narrow, assays were performed by preincubating parasites with supernatants and then by resuspending them in DMEM-cysteine before the adhesion assays. Incubation of strain WB with acid supernatants (pH 4) (DMEM:supernatant=1:1) during 1 hr produced a reduction of adhesion from 15% for MRS to around 3% for all the strains under study (FIG. 7A). Neutralization of supernatants (pH 7) eliminated the inhibitory effect and an increase in adhesion was found (FIG. 7B).

The results obtained by incubating WB strain with supernatants of La10 strain adjusted to different pH are shown in FIG. 8A. No differences as compared to the MRS control at pH 4 and 5 were found but adhesion was found to be higher at a pH of 6 and 7.

Dilution of acid supernatants with MRS produced an increase in pH and adhesion was reduced with supernatants diluted ⅛ (relative concentration 0.125, pH 4.07, FIG. 8B).

Figure 9:
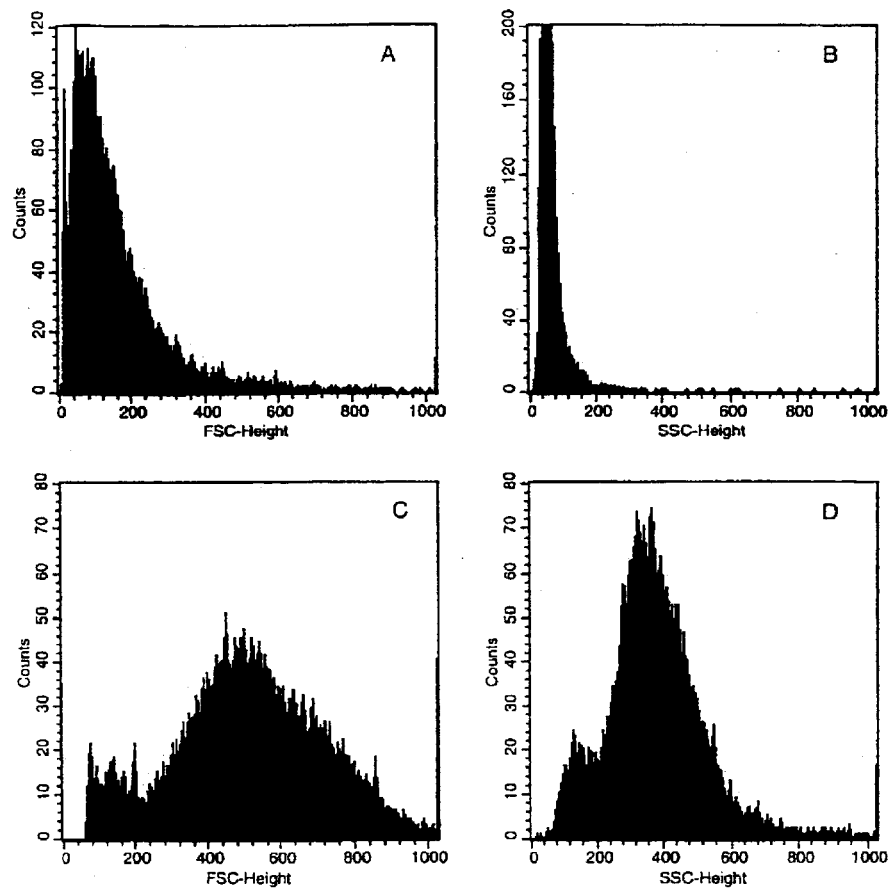
FIG. 9 shows a low cytometric analysis of suspensions of strain WB 1 incubated during 1 h at 37° with MRS acidified to pH 5 (DMEM: MRS=1:1)
Figure 10:
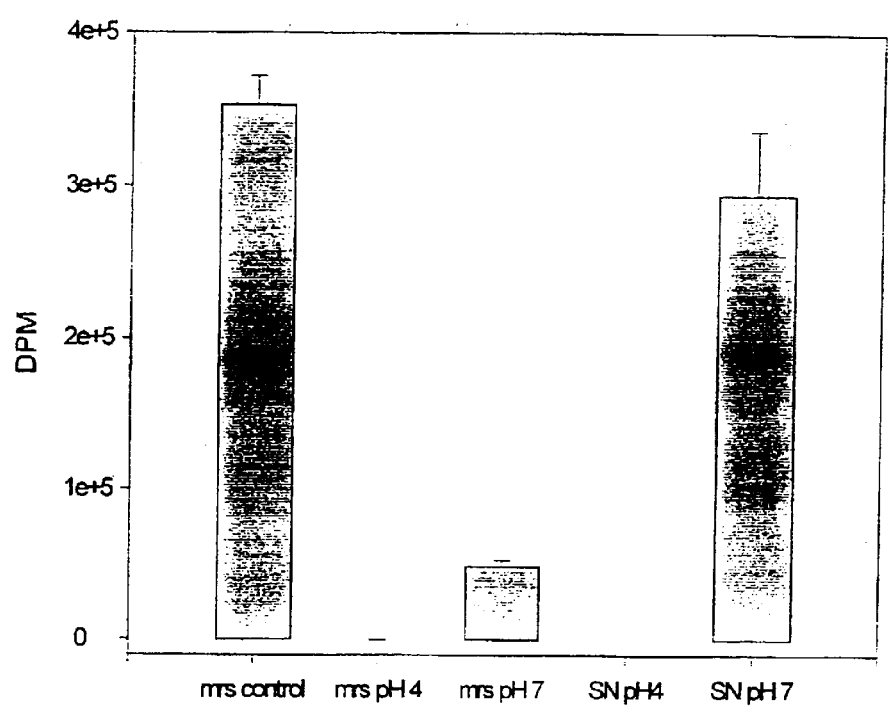
FIG. 10 shows the results of an inoculation of parasites preincubated at pH 4 or 7 in TYI-S-33 medium with 100 μCi of $^3$H adenine.

Flow cytometric analysis of suspensions of strain WB 1 incubated for 1 hr at 37° with MRS acidified to pH 5 (DMEM MRS=1:1) showed differences in size. (FSC) and cytoplasmatic complexity (SSC) (FIG. 9). Inoculation of parasites preincubated at pH 4 or 7 in TYI-S-33 medium with 100 $\mu$Ci of $^3$H adenine showed differences in incorporation (FIG. 10). Low adenine incorporation was detected at pH 4 after 28 hrs of incubation in both MRS and supernatants samples. Although some parasites were attached to the bottle walls, they were not motile. MRS broth, acidified to pH 4.05 and neutralized, showed values of DPM representing less than 20% of the control. For neutralized supernatants of strain La10 values were around 80% of the control and differences were significant at 0.09 level. Big aggregates of parasites were found at pH 7 in both MRS and supernatants.

Figure 4:
FIG. 4 shows the microvilli damage at the epithelial cell brush border by *Giardia intestinalis*.

The results for *Giardia* adhesion to different cell lines (FIGS. 1 and 2) suggests that non specific attachment seems to be an important feature of this system, since no significant differences were found between differentiated cells (Caco-2 with different times in culture) and undifferentiated cells (HT-29). Furthermore, adhesion to plastic surfaces was very high. Adhesion of trophozoites to Caco-2 monolayers obviously produced microvilli damage (FIG. 4).

Experiments of exclusion of parasites with a washing step after bacterial adhesion led to a damage of the monolayer resulting in exclusion values that did not seem to be authentic. The degree of damage depended on the washing solution ranging from effacing of microvilli with DMEM-cys (scanning electron microscopy) to cell detachment with PBS. Taking into account the above findings, assays were performed, wherein monolayers were preincubated with bacteria suspended in DMEM-cys but without a washing step prior to the addition of the parasites. Another series of experiments was performed by coincubating parasites and bacteria with Caco-2 cells. The results obtained (FIG. 5) are compatible with "active" attachment of trophozoites mediated by flagella motility and contractile elements. Lactic acid bacteria, being non motile, could not compete with parasites for attachment.

Concerning the action of supernatants of lactic acid bacteria cultures, they have been shown to inhibit *Giardia* adhesion. Without to be bound to any theory it is deemed that this inhibitory effect may be attributed mainly to particular organic acids secreted by the lactic acid bacteria.

A preincubation of parasites with MRS acidified with lactic acid showed dramatic changes in cellular size and cytoplasmatic complexity and adhesion to Caco-2 cells was reduced both for supernatants and MRS controls. In these conditions, the viability of parasites is highly affected, as is shown in experiments wherein treated parasites are inoculated in fresh TYI-S-33.

After contact with lactate at pH 4 growth of parasites essentially stopped although some parasites were able to attach to the bottle walls. It seemed that under these conditions lactic acid is lethal to *Giardia*. At pH 7, the inhibitory effect of lactate is still present and differences between acidified MRS and supernatant of La10 strain could be explained by assuming differences in lactate concentration due to the differences in buffer capability between fresh MRS and spent supernatants.

Figure 8:
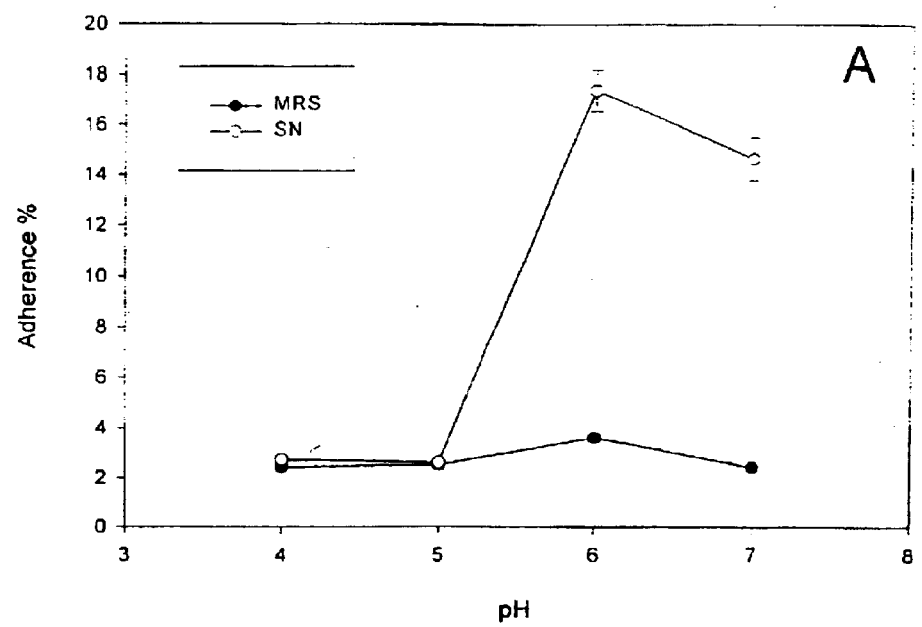
FIG. 8A shows the results obtained by incubating WB strain with supernatants of La10 strain adjusted to different pH.
FIG. 8B shows the results of diluting acid supernatants with MRS.
Figure 8:
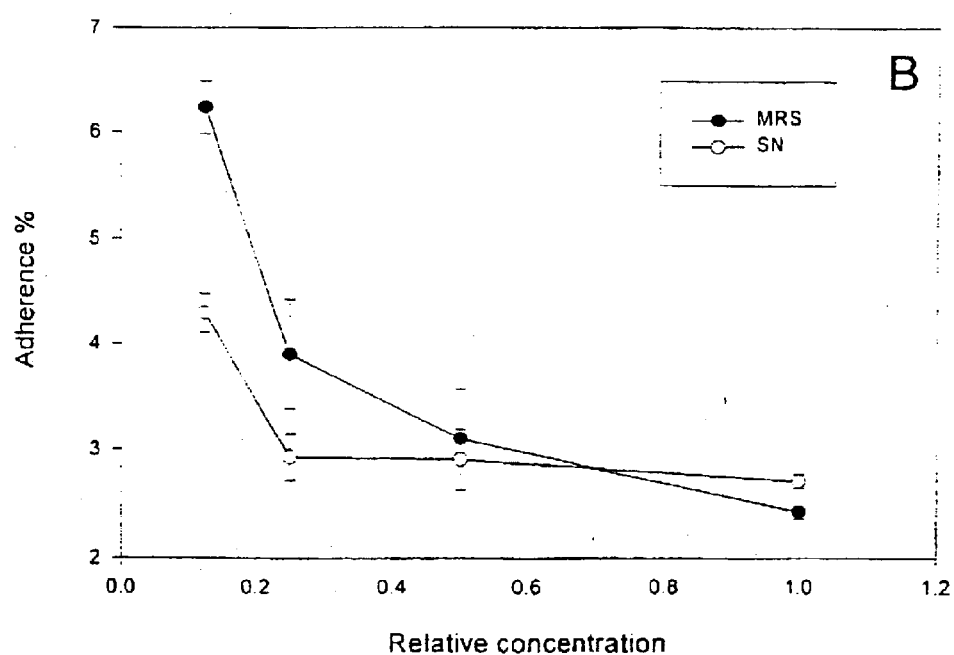

*Giardia* aggregates were formed during preincubation of parasites with supernatants and they might account for the high values of adhesion founded at pH 6 and 7 (FIG. 8). As stated before, the main mechanisms for *Giardia* adhesion requires parasite viability, though adhesion of death protozoa could be shown after treatment of trophozoites with supernatants at pH 4. These parasites were not able to multiply and thus will not be effective in producing parasitosis. Furthermore, neutralized supernatants of cultures of lactic acid bacteria retarded *Giardia* growth and produced aggregates unable to attach.

In view of the above experimental results it becomes clear that the lactic acid bacteria to be used according to the present invention may be successfully applied for the treatment or prophylaxis of giardiasis.

It should be understood that various changes and modifications to the presently preferred embodiments described herein will be apparent to those skilled in the art. Such changes and modifications can be made without departing from the spirit and scope of the present invention and without diminishing its intended advantages. It is therefore intended that such changes and modifications be covered by the appended claims.

What is claimed is:

1. A method for the treatment of a disorder associated with the colonization of the gut by *Giardia* intestinalis comprising the step of administering to a patient in need of same a therapeutically effective amount of lactic acid bacteria or Bifidobacteria, selected from the group consisting of NCC90 (I-2332), NCC 189 (I-2333), and NCC 200 (I-2334).

2. The method according to claim 1, wherein the bacterium is contained in a carrier in an amount of from $10^6$ to $10^{12}$ cfu/g.

3. The method according to claim 1, wherein the bacterium is contained in a food composition.

4. The method according to claim 3, wherein the food composition is selected from the group consisting of milk, yogurt, curd, cheese, fermented milks, milk based fermented products, ice-creams, fermented cereal based products, milk based powders, infant formulate and pet food.

5. A method of reducing the risk of a disorder associated with the colonization of the gut by *Giardia intestinalis* comprising the step of administering a lactic acid bacteria or Bifidobacteria, selected from the group consisting of NCC90 (I-2332), NCC 189 (I-2333), and NCC 200 (I-2334).

6. The method according to claim 1, including an ingestable carrier that is chosen from the group consisting of a food composition and a pharmaceutical composition.

7. The method according to claim 6, wherein the food composition is selected from the group consisting of milk, yogurt, curd, cheese, fermented milks, milk based fermented products, ice-creams, fermented cereal based products, milk based powders, infant formulae and pet food.

8. The method according to claim 6, wherein the pharmaceutical composition is in a form selected from the group consisting of tablet, liquid bacterial suspension, dried oral supplement, wet oral supplement, dry tube feeding and a wet tube feeding.

9. The method according to claim 5, wherein the bacterium is contained in the carrier in an amount of from $10^6$ to $10^{12}$ cfu/g.

10. The method according to claim 5, including an ingestable carrier chosen from the group consisting of a food composition and a pharmaceutical composition.

11. The method according to claim 10, wherein the food composition is selected from the group consisting of milk, yogurt, curd, cheese, fermented milks, milk based fermented products, ice-creams, fermented cereal based products, milk based powders, milk based powders, infant formulae and pet food.

12. The method to claim 10, wherein the pharmaceutical composition is in a form selected from the group consisting of a tablet, liquid bacterial suspension, dried oral supplement, wet oral supplement, dry tube feeding and a wet tube feeding.

* * * * *